United States Patent [19]

Carter et al.

[11] Patent Number: 5,135,681
[45] Date of Patent: Aug. 4, 1992

[54] SUBSTITUTED CARBOXYMETHOXYSUCCINIC ACID CORROSION INHIBITORS

[75] Inventors: Charles G. Carter, Silver Spring; Vladimir Jovancicevic, Columbia, both of Md.

[73] Assignee: W. R. Grace & Co.-Conn., New York, N.Y.

[21] Appl. No.: 782,362

[22] Filed: Oct. 24, 1991

[51] Int. Cl.$^5$ .............................................. C23F 11/12
[52] U.S. Cl. ........................... 252/389.62; 252/396; 252/389.61; 422/17
[58] Field of Search ............. 252/396, 389.62, 389.61; 422/17

[56] References Cited

U.S. PATENT DOCUMENTS

| | | | |
|---|---|---|---|
| 2,638,449 | 5/1953 | White et al. | 252/515 A |
| 3,954,858 | 5/1976 | Lamberti et al. | 562/583 |
| 4,066,687 | 1/1978 | Nelson et al. | 562/583 |
| 4,663,071 | 5/1987 | Bush et al. | 252/174.19 |
| 4,898,687 | 2/1990 | Parker et al. | 252/389.61 |

FOREIGN PATENT DOCUMENTS 2513735 10/1975 Fed. Rep. of Germany .
1389732 4/1975 United Kingdom .

*Primary Examiner*—Deborah L. Kyle
*Assistant Examiner*—Valerie Fee
*Attorney, Agent, or Firm*—James P. Barr

[57] ABSTRACT

A method is disclosed for inhibiting corrosion of a ferrous based metal in contact with an aqueous system comprising incorporating into the aqueous system an effective amount of a substituted carboxymethoxysuccinic acid selected from the group consisting of compounds having the formula:

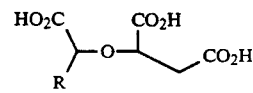

wherein R is $-(CHOH)_nCH_2OH$, $-(CHOH)_mCO_2H$ or $-(CHOH)_r(CHOR')CO_2H$ and R' is $CH(CO_2H)CH_2CO_2H$; n is 1,2,3 or 4; m is 1,2,3, or 4; r is 1,2, or 3; and water soluble salts thereof.

16 Claims, No Drawings

SUBSTITUTED CARBOXYMETHOXYSUCCINIC ACID CORROSION INHIBITORS

FIELD OF THE INVENTION

The present invention relates to the inhibition and prevention of corrosion of ferrous-based metals which are in contact with an aqueous system. More particularly, this invention relates to a method wherein a substituted carboxymethoxysuccinic acid is added to the aqueous system in an amount effective to inhibit corrosion of the ferrous based metal.

BACKGROUND OF THE INVENTION

Iron and iron-based metal-containing alloys, such as mild steel, are well-known materials used in constructing the apparatus of aqueous systems. In these systems water circulates, contacts the ferrous-based metal surface, and may be concentrated, such as by evaporation of a portion of the water from the system. Even though such metals are readily subject to corrosion in such environments, they are used over other metals due to their strength and availability.

It is known that various materials which are naturally or synthetically occurring in the aqueous systems, especially systems using water derived from natural resources such as seawater, rivers, lakes and the like, attack ferrous-based metals, the term "ferrous-based metals", as used herein, shall mean iron metal and metal alloys containing iron therein, i.e., ferrous metals. Typical devices in which the ferrous-metal parts are subject to corrosion include evaporators, single and multi-pass heat exchangers, cooling towers, and associated equipment and the like. As the system water passes through or over the device, a portion of the system water evaporates causing a concentration of the dissolved materials contained in the system. These materials approach and reach a concentration at which they may cause severe pitting and corrosion which eventually requires replacement of the metal parts. Various corrosion inhibitors have been previously used.

Chromates and inorganic phosphates or polyphosphates have been used in the past to inhibit the corrosion of metals which is experienced when the metals are brought into contact with water. The chromates, though effective, are highly toxic and, consequently, present handling and disposal problems. Phosphates are nontoxic. However, due to the limited solubility of calcium phosphate it is difficult to maintain adequate concentrations of phosphates in many instances. The polyphosphates are also relatively non-toxic, but tend to hydrolyze to form orthophosphate which in turn like phosphate itself can create scale and sludge problems in aqueous systems (e.g. by combining with calcium in the system to form calcium phosphate). Moreover, where there is concern over eutrophication of receiving waters, excess phosphate compounds can provide disposal problems as nutrient sources. Borates, nitrates, and nitrites have also been used for corrosion inhibition. These too can serve as nutrients in low concentrations, and/or represent potential health concerns at high concentrations.

In addition, environmental considerations have also recently increased concerns over the discharge of other metals such as zinc, which previously were considered acceptable for water treatment.

Much recent research has been concerned with the development of organic corrosion inhibitors which can reduce reliance on the traditional inorganic inhibitors. Among the organic inhibitors successfully employed are numerous organic phosphonates. These compounds may generally be used without detrimentally interfering with other conventional water treatment additives. These organic phosphonates, however, can be degraded to form orthophosphate, raising concern over eutrophication of receiving waters. This has led to restriction on the discharge of organic phosphonates by some regulatory bodies. Despite a number of reports of non-phosphorus organic corrosion inhibitors, no agent of this type has enjoyed wide commercial acceptance.

There is a continuing need, therefore, for safe and effective water treatment agents which can be used to control corrosion. In particular, there is a need for treatment agents that are based on non-phosphorus-containing organic corrosion inhibitors.

SUMMARY OF THE INVENTION

It is an object of this invention to provide a method of inhibiting the corrosion of a ferrous-based metal in contact with an aqueous system.

In accordance with the present invention there has been provided a method of inhibiting corrosion of a ferrous-based metal in contact with an aqueous system, wherein a substituted carboxymethoxysuccinic acid is added to the aqueous system in an amount effective to inhibit corrosion.

DETAILED DESCRIPTION

This invention is directed to the use of certain substituted carboxymethoxysuccinic acid compounds as corrosion control agents for treating aqueous systems. The substituted carboxymethoxysuccinic compounds of this invention have the general formula:

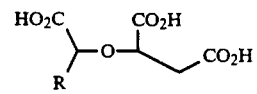

wherein R is —(CHOH)$_n$CH$_2$OH, —(CHOH)$_n$CO$_2$H or —(CHOH)$_r$ (CHOR')CO$_2$H and R' is CH(CO$_2$H)CH$_2$CO$_2$H; n is 1,2,3 or 4; m is 1,2,3, or 4; r is 1,2 or 3; and water soluble salts thereof. Preferred compounds for use in this invention are those having the above formula wherein R is —(CHOH)$_r$(CHOR')CO$_2$H and r is 2 or 3 or wherein R is —(CHOH)$_m$CO$_2$H and m is 2 or 3.

The substituted carboxymethoxysuccinic acid compounds of this invention can be prepared by reacting an α,β-unsaturated carboxylic acid, such as maleic acid, with an α-hydroxycarboxylic acid in the presence of an alkaline earth metal hydroxide, preferably calcium hydroxide. This procedure is more fully described in U.S. Pat No. 3,954,858 to Lamberti et al which is incorporated herein by reference in its entirety.

These substituted carboxymethoxysuccinic acid compounds have been found to be effective for inhibiting corrosion in aqueous systems. Thus, in accordance with this invention, corrosion of metals, which are in contact with an aqueous system, may be prevented or inhibited by adding to the system a corrosion inhibiting amount of the substituted carboxymethoxysuccinic acid compounds of this invention, or their water soluble salts.

The precise dosage of the corrosion inhibiting agents of this invention depends, to some extent, on the nature of the aqueous system in which it is to be incorporated and the degree of protection desired. In general, however, the concentration of the substituted carboxymethoxysuccinic acid compound maintained in the system can be from about 0.1 to about 1,000 ppm. Within this range, generally low dosages of about 200 ppm or less are preferred, with a dosage of about 100 ppm or less being most preferred for many aqueous systems, such as for example, many open recirculating cooling water systems. Typically dosages of about 0.5 ppm or more are preferred, with a dosage of about 2 ppm or more being most preferred. The exact amount required with respect to a particular aqueous system can be readily determined by one of ordinary skill in the art in conventional manners. As is typical of most aqueous systems, the pH is preferably maintained at 7 or above, and is most preferably maintained at 8 or above.

The corrosion inhibiting compositions of this invention may be added to the system water by any convenient mode, such as by first forming a concentrated solution of the treating agent with water, preferably containing between 1 and 50 total weight percent of the substituted carboxymethoxysuccinic acid compound, and then feeding the concentrated solution to the system water at some convenient point in the system. In many instances, the treatment compositions may be added to the make-up water or feed water lines through which water enters the system. For example, an injection calibrated to deliver a predetermined amount periodically or continuously to the make-up water may be employed.

The present invention is particularly useful in the treatment of cooling water systems which operate at temperatures between 60° and 200° F., particularly open recirculating cooling water systems which operate at temperatures of from about 80° F. to 150° F.

It will be appreciated that while the chemical corrosion inhibiting compositions of this invention may be used as the sole corrosion inhibitor for the aqueous system, other conventional water treatment compositions customarily employed in aqueous systems may advantageously be used in combination with the claimed treatment agents. Thus, other water treatment additives which may be used include, but are not limited to, biocides, scale inhibitors, chelants, sequestering agents, dispersing agents, other corrosion inhibitors, polymeric agents (e.g. copolymers of 2-acrylamido-2-methyl propane sulfonic acid and methacrylic acid or polymers of acrylic acid and methacrylic acid), and the like.

Without further elaboration, it is believed that one of skill in the art, using the preceding detailed description, can utilize the present invention to its fullest extent.

The following examples are provided to illustrate the invention in accordance with the principles of this invention, but is not to be construed as limiting the invention in any way except as indicated in the appended claims.

EXAMPLE 1

O-Succinyl Gluconic Acid (OSG)

Sodium hydroxide (3.2 g., 80 mmole) and γ-gluconolactone (8.9 g., 50 mmole) were dissolved in 30 ml. distilled water. Maleic acid (5.8 g., 50 mmole) and calcium hydroxide (3.0 g., 40 mmole) were added. The resulting white slurry was heated to reflux for four hours. At this point, the reaction mixture was a hazy, yellow solution. An additional 1.16 g. of maleic acid (total 6.96 g., 60 mmole), 0.72 g. of sodium hydroxide (total 3.92 g., 98 mmole) and 0.3 g. of calcium hydroxide (total 3.3 g., 44 mmole) were added and the mixture was heated to reflux for an additional 2-3 hours.

The reaction was filtered through an 0.22 micron filtration system. Quantitative proton NMR analysis of the reaction product indicated an 85% yield of the desired OSG and 15% unreacted gluconic acid. This corresponds to a mixture that contains, on a weight basis, 90% OSG and 10% gluconic acid.

EXAMPLE 2

O-Succinyl Saccharic Acid (OSS)

Sodium hydroxide (4.0 g., 100 mmole) and saccharic acid, monopotassium salt (12.4 g., 50 mmole) were dissolved in 30 ml. distilled water. Maleic acid (6.96 g., 60 mmole) and calcium hydroxide (2.96 g., 40 mmole) were added under a nitrogen atmosphere. The pH was adjusted to 12 with sodium hydroxide (0.7 g., 17.5 mmole). The reaction mixture was heated to reflux for 18 hours.

A slurry of 2.4 g. distilled water, 0.8 g. sodium hydroxide (total 5.5 g., 138 mmole) and 2.3 g. maleic acid (total 9.3 g., 80 mmole) was added to the reaction. It was allowed to continue refluxing for an additional 43 hours while checking periodically by proton NMR.

Proton NMR analysis of the reaction product indicated a 75% yield of the desired OSS and 25% unreacted saccharic acid. This corresponds to a mixture that contains, on a weight basis, 82% OSS and 18% saccharic acid.

EXAMPLE 3

The corrosion inhibitor activity of several selected compounds of this invention was demonstrated by the an Aerated Bottle Test using the following procedure and two standard corrosive waters with the following compositions:

Water A
 12.8 ppm $CaCl_2$
 54.6 ppm $MgSO_4$
 110.7 ppm $CaSO_4.2H_2O$
 175.7 ppm $NaHCO_3$
Water B
 25.6 ppm $CaCl_2$
 109.2 ppm $MgSO_4$
 221.4 ppm $CaSO_4.2H_2O$
 351.4 ppm $NaHCO_3$ Mild steel coupons (4.5 in×0.5 in) were immersed in 15% hydrochloric acid for 15 minutes, then rinsed sequentially in saturated sodium bicarbonate solution, distilled water and isopropanol, dried and stored in a desiccator. They were weighed prior to being used in the corrosion test.

The desired amount of corrosion inhibitor was dissolved in 850 ml of one of the standard corrosive waters listed above. The solution was heated in a thermostatted bath at 55° C. After the temperature had equilibrated the pH of the solution is adjusted to 8.5. Two coupons were suspended in the solution and air was passed into the solution at 250 ml/min. After 48 hours, the coupons were removed and cleaned with steel wool, rinsed, dried, and weighed again. The rate of corrosion was calculated from the weight loss and was expressed in mils per year (mpy). Corrosion Inhibition was expressed as the reduction in the rate of corrosion relative to an untreated blank calculated according to the formula:

% Corrosion Inhibition =

$$\frac{(\text{Corrosion Rate of Untreated Blank} - \text{Corrosion Rate with Treatment}) \times 100}{\text{Corrosion Rate of Untreated Blank}}$$

For purposes of this invention, an effective corrosion inhibitor will reduce the corrosion rate by at least 80% compared to the blank.

The results shown in Table 1 demonstrate that the substituted carboxymethoxysuccinic acid compounds of this invention were effective corrosion inhibitors. In contrast, the comparison compounds, ODS, CMOS and Asp-MA were not effective corrosion inhibitors, even when present at a high concentration. The lack of corrosion inhibition activity of the comparison compounds, which can also be prepared by the method of Lamberti, highlights the unpredictability of the relationship between structure and corrosion inhibition. The differences in activity seen between the substituted carboxymethoxysuccinic acid compounds of the present invention and the comparison compounds listed in Table I were surprising in light of the close structural similarity.

TABLE 1

| CORROSION INHIBITION - AERATED BOTTLE TEST | | | |
|---|---|---|---|
| | Dosage | % Corrosion Inhibition | |
| Inhibitor | (ppm) | Water A | Water B |
| OSS | 100 | 98 | 91 |
| | 75 | 98 | 82 |
| | 50 | 47 | — |
| | 40 | 21 | — |
| OSG | 200 | 98 | 88 |
| | 150 | 97 | 66 |
| | 100 | 73 | — |
| Gluconic Acid* | 150 | 33 | 32 |
| | 100 | 30 | — |
| ODS* | 150 | 39 | 66 |
| CMOS* | 200 | 0 | 29 |
| | 150 | 19 | 38 |
| Asp-MA* | 200 | 9 | 56 |
| | 150 | 11 | 48 |
| | 100 | — | 49 |

*comparison compounds

We claim:

1. A method of inhibiting corrosion of a ferrous-based metal in contact with an aqueous system which consists essentially of incorporating into the aqueous system, in an amount effective to inhibit corrosion, a substituted carboxymethoxysuccinic acid or water soluble salts thereof.
2. The method according to claim 1 wherein a concentration of from 0.1 ppm to 1,000 ppm of said compound is maintained in the aqueous system.
3. The method according to claim 1 wherein a concentration of from 0.5 to 200 ppm of said compound is maintained in the aqueous system.
4. The method according to claim 1 wherein a concentration of from 0.5 ppm to 100 ppm of said compound is maintained in the aqueous system.
5. The method according to claim 1 wherein said substituted carboxymethoxysuccinic acid is selected from the group consisting of compounds having the formula:

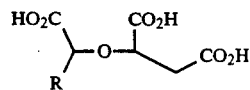

wherein R is $-(CHOH)_n CH_2OH$, $-(CHOH)_m CO_2H$ or $-(CHOH)_r (CHOR')CO_2H$ and R' is $CH(CO_2H)CH_2CO_2H$; n is 1,2,3 or 4; m is 1,2,3, or 4; r is 1,2, or 3; and water soluble salts thereof.
6. The method according to claim 5 where R is $-(CHOH)_n CH_2OH$ and n is 1,2,3 or 4.
7. The method according to claim 6 wherein n is 3.
8. The method according to claim 7 wherein said salt is a sodium salt.
9. The method according to claim 5 wherein R is $-(CHOH)_n CO_2H$ and m is 1,2,3 or 4.
10. The method according to claim 9 wherein m is 3.
11. The method according to claim 10 wherein said salt is a sodium salt.
12. The method according to claim 5 wherein R is $-(CHOH)_r(CHOR')CO_2H$.
13. The method according to claim 12 wherein r is 2.
14. The method according to claim 12 wherein said salt is a sodium salt.
15. The method according to claim 1 wherein said salts are alkali metal salts.
16. The method according to claim 15 wherein said salts are sodium salts.

* * * * *